United States Patent
Kim et al.

(10) Patent No.: US 11,749,414 B2
(45) Date of Patent: *Sep. 5, 2023

(54) SELECTING SPEECH FEATURES FOR BUILDING MODELS FOR DETECTING MEDICAL CONDITIONS

(71) Applicant: Canary Speech, LLC, Provo, UT (US)

(72) Inventors: Jangwon Kim, Los Angeles, CA (US); Namhee Kwon, Manhattan Beach, CA (US); Henry O'Connell, Spanish Fork, UT (US); Phillip Walstad, Provo, UT (US); Kevin Shengbin Yang, Boston, MA (US)

(73) Assignee: CANARY SPEECH, LLC, Spanish Fork, UT (US)

( * ) Notice: Subject to any disclaimer, the term of this patent is extended or adjusted under 35 U.S.C. 154(b) by 143 days.

This patent is subject to a terminal disclaimer.

(21) Appl. No.: 17/151,632

(22) Filed: Jan. 18, 2021

(65) Prior Publication Data

US 2021/0142917 A1 May 13, 2021

Related U.S. Application Data

(63) Continuation of application No. 16/189,997, filed on Nov. 13, 2018, now Pat. No. 10,896,765, which is a
(Continued)

(51) Int. Cl.
*G10L 15/02* (2006.01)
*G10L 15/22* (2006.01)
(Continued)

(52) U.S. Cl.
CPC ........... *G16H 80/00* (2018.01); *A61B 5/1123* (2013.01); *A61B 5/4088* (2013.01);
(Continued)

(58) Field of Classification Search
CPC ......... G10L 15/00; G10L 15/07; G10L 15/26; G10L 15/265; G10L 25/00; G10L 25/63; A61B 5/00; A61B 5/0004; G06F 3/16
See application file for complete search history.

(56) References Cited

U.S. PATENT DOCUMENTS

| 6,067,516 A | 5/2000 | Levay et al. |
| 6,804,654 B2 | 10/2004 | Kobylevsky et al. |

(Continued)

FOREIGN PATENT DOCUMENTS

| AU | 5315699 A | 2/2000 |
| WO | 2015/107747 | 7/2015 |

(Continued)

OTHER PUBLICATIONS

Pérez-Espinosa, Humberto, Carlos A. Reyes-Garcia, and Luis Villasenor-Pineda. "Acoustic feature selection and classification of emotions in speech using a 3D continuous emotion model." Biomedical Signal Processing and Control 7.1 (2012): 79-87.*

(Continued)

*Primary Examiner* — Paras D Shah
(74) *Attorney, Agent, or Firm* — Kunzler Bean & Adamson

(57) ABSTRACT

A mathematical model may be trained to diagnose a medical condition of a person by processing acoustic features and language features of speech of the person. The performance of the mathematical model may be improved by appropriately selecting the features to be used with the mathematical model. Features may be selected by computing a feature selection score for each acoustic feature and each language feature, and then selecting features using the scores, such as by selecting features with the highest scores. In some implementations, stability determinations may be computed for each feature and features may be selected using both the feature selection scores and the stability determinations. A (Continued)

mathematical model may then be trained using the selected features and deployed. In some implementations, prompts may be selected using computed prompt selection scores, and the deployed mathematical model may be used with the selected prompts.

20 Claims, 8 Drawing Sheets

Related U.S. Application Data continuation of application No. 15/973,498, filed on May 7, 2018, now Pat. No. 10,152,988.

(60) Provisional application No. 62/614,192, filed on Jan. 5, 2018, provisional application No. 62/502,584, filed on May 5, 2017.

(51) Int. Cl.
| | |
|---|---|
| *G10L 15/06* | (2013.01) |
| *G16H 80/00* | (2018.01) |
| *G16H 50/20* | (2018.01) |
| *G10L 25/66* | (2013.01) |
| *G16H 10/20* | (2018.01) |
| *A61B 5/11* | (2006.01) |
| *G06N 20/10* | (2019.01) |
| *G16H 40/67* | (2018.01) |
| *G06N 7/01* | (2023.01) |
| *G16H 50/50* | (2018.01) |
| *A61B 5/00* | (2006.01) |
| *G06N 3/08* | (2023.01) |
| *G06F 111/10* | (2020.01) |

(52) U.S. Cl.
CPC .......... *A61B 5/4803* (2013.01); *A61B 5/7267* (2013.01); *G06N 3/08* (2013.01); *G06N 7/01* (2023.01); *G06N 20/10* (2019.01); *G10L 25/66* (2013.01); *G16H 10/20* (2018.01); *G16H 40/67* (2018.01); *G16H 50/20* (2018.01); *G16H 50/50* (2018.01); *G06F 2111/10* (2020.01); *G10L 15/02* (2013.01); *G10L 15/063* (2013.01); *G10L 15/22* (2013.01)

(56) References Cited

U.S. PATENT DOCUMENTS

| | | | |
|---|---|---|---|
| 7,315,821 B2 | 1/2008 | Monchi et al. | |
| 7,454,350 B2 | 11/2008 | Silverman | |
| 8,494,857 B2 | 7/2013 | Pakhomov | |
| 8,784,311 B2 | 7/2014 | Shrivastav et al. | |
| 9,055,861 B2 | 6/2015 | Oh et al. | |
| 9,058,816 B2 | 6/2015 | Lech et al. | |
| 9,295,423 B2 | 3/2016 | Sethi | |
| 9,390,167 B2 | 7/2016 | Mont-Reynaud et al. | |
| 9,514,281 B2 | 12/2016 | Hirst et al. | |
| 9,579,056 B2 | 2/2017 | Rosenbek et al. | |
| 9,763,617 B2 | 9/2017 | Quatieri et al. | |
| 9,936,914 B2 | 4/2018 | Quatieri, Jr. et al. | |
| 10,152,988 B2 | 12/2018 | Kim et al. | |
| 10,311,980 B2 | 6/2019 | Kim et al. | |
| 10,796,715 B1 * | 10/2020 | Berisha | A61B 5/4842 |
| 2003/0105638 A1 | 6/2003 | Taira | |
| 2003/0115214 A1 | 6/2003 | Essar et al. | |
| 2004/0210159 A1 | 10/2004 | Kibar | |
| 2007/0226012 A1 | 9/2007 | Salgado et al. | |
| 2009/0191521 A1 | 7/2009 | Paul et al. | |
| 2010/0286490 A1 | 11/2010 | Koverzin | |
| 2011/0319384 A1 | 12/2011 | Eriksson et al. | |
| 2012/0116186 A1 | 5/2012 | Shrivastav et al. | |
| 2012/0277594 A1 | 11/2012 | Pryor | |
| 2012/0310670 A1 | 12/2012 | Pruitt | |
| 2014/0073993 A1 | 3/2014 | Poellabauer et al. | |
| 2014/0113263 A1 | 4/2014 | Jarrell et al. | |
| 2014/0279729 A1 | 9/2014 | Delaney et al. | |
| 2014/0365411 A1 | 12/2014 | Beigi et al. | |
| 2015/0318002 A1 | 11/2015 | Karam et al. | |
| 2016/0004831 A1 | 1/2016 | Carlson et al. | |
| 2016/0022193 A1 | 1/2016 | Rau et al. | |
| 2016/0135737 A1 | 5/2016 | Bowers et al. | |
| 2016/0140986 A1 | 5/2016 | Bowers et al. | |
| 2016/0262680 A1 | 9/2016 | Martucci et al. | |
| 2016/0278684 A1 | 9/2016 | Kozloski et al. | |
| 2016/0335399 A1 | 11/2016 | Vancho | |
| 2017/0007167 A1 | 1/2017 | Kostic et al. | |
| 2017/0039045 A1 | 2/2017 | Abrahami et al. | |
| 2017/0053665 A1 | 2/2017 | Quatieri, Jr. et al. | |
| 2017/0076740 A1 | 3/2017 | Feast et al. | |
| 2017/0086672 A1 | 3/2017 | Tran | |
| 2017/0119302 A1 | 5/2017 | Rosenbek et al. | |
| 2017/0125034 A1 | 5/2017 | Kakadiaris et al. | |
| 2017/0249438 A1 | 8/2017 | Jain et al. | |
| 2017/0300648 A1 | 10/2017 | Charlap | |
| 2019/0073885 A1 | 3/2019 | Bess et al. | |
| 2019/0311815 A1 | 10/2019 | Kim et al. | |

FOREIGN PATENT DOCUMENTS

| | | |
|---|---|---|
| WO | 2016/028495 | 2/2016 |
| WO | 2016028495 A1 | 2/2016 |
| WO | 2017/083480 | 5/2017 |

OTHER PUBLICATIONS

Räsänen, Okko, and Jouni Pohjalainen. "Random subset feature selection in automatic recognition of developmental disorders, affective states, and level of conflict from speech." Interspeech. 2013.*
Firdos, Seema, and K. Umarani. "Disordered voice classification using SVM and feature selection using GA." 2016 Second International Conference on Cognitive Computing and Information Processing (CCIP). IEEE, 2016.*
Application No. PCT/US18/31460, International Search Report and Written Opinion, dated Jul. 11, 2018.
U.S. Appl. No. 15/973,498, Office Action, dated Jul. 6, 2018.
Application No. PCT/US18/31461, International Search Report and Written Opinion, dated Aug. 2, 2018.
Lopez-De-Ipina et al., On Automatic Diagnosis of Alzheimer's Disease Based on Spontaneous Speech Analysis and Emotional Temperature, Cognitive Computation, Aug. 2013, Springer US, US.
Konig et al., Automatic speech analysis for the assessment of patients with predementia and Alzheimer's disease, Alzheimer's & Dementia, 2015, Elsevier Inc., NL.
Khodabakhsh et al, Analysis of Speech-Based Measures for Detecting and Monitoring Alzheimer's Disease, Data Mining in Clinical Medicine, Nov. 2014, Humana Press, New York, NY.
U.S. Appl. No. 15/973,498, Notice of Allowance, dated Oct. 31, 2018.
U.S. Appl. No. 15/973,504, Notice of Allowance, dated Apr. 3, 2019.
U.S. Appl. No. 15/973,504, Office Action, dated Aug. 8, 2018.
Application No. 18794955.7, Extended European Search Report, dated Dec. 8, 2020.
Application No. 18794118.2, Supplementary European Search Report and Written Opinion, dated Jan. 18, 2021.
JP Patent Application No. 2020-511875, Notice of Allowance, dated Dec. 4, 2022.
JP Patent Application No. 2020-511874, Notice of Allowance, dated Dec. 4, 2022.
U.S. Appl. No. 17/827,970, Notice of Allowance dated Apr. 10, 2023.
Gonzalez, Jose A et al. "Direct Speech Reconstruction From Articulatory Sensor Data by Machine Learning." IEEE/ACM Transactions on Audio, Speech and Language Processing, vol. 25, No. 12, Dec. 2017.

* cited by examiner

| Prompt ID | Prompt |
|---|---|
| concussion1 | What venue are we at today? |
| concussion2 | What team did you play last week? |
| concussion3 | Did your team win its last game? |
| ... | ... |
| alzheimers1 | How are you today? |
| alzheimers2 | How many states have you lived in? |
| alzheimers3 | What do you do for a living? |
| ... | ... |

Fig. 4

| Person ID | Diagnosis | Prompt ID | Speech Data |
|---|---|---|---|
| john_smith_123 | Concussion (mild) | concussion1 | 201804121001.wav |
| john_smith_123 | Concussion (mild) | concussion2 | 201804121002.wav |
| john_smith_123 | Concussion (mild) | concussion3 | 201804121003.wav |
| ... | ... | ... | ... |
| jane_doe_456 | Concussion (moderate) | concussion1 | 201804122001.wav |
| jane_doe_456 | Concussion (moderate) | concussion2 | 201804122002.wav |
| jane_doe_456 | Concussion (moderate) | concussion3 | 201804122003.wav |
| ... | ... | ... | ... |

Fig. 3

SELECTING SPEECH FEATURES FOR BUILDING MODELS FOR DETECTING MEDICAL CONDITIONS

CLAIM OF PRIORITY

This patent application is a continuation of U.S. patent application Ser. No. 16/189,997 entitled "SELECTING SPEECH FEATURES FOR BUILDING MODELS FOR DETECTING MEDICAL CONDITIONS" and filed on Nov. 13, 2018 for Jangwon Kim, et al., which is a continuation of U.S. patent application Ser. No. 15/973,498 entitled "SELECTING SPEECH FEATURES FOR BUILDING MODELS FOR DETECTING MEDICAL CONDITIONS" and filed on May 7, 2018 for Jangwon Kim, et al., which claims the benefit of U.S. Provisional Patent Application No. 62/502,584, filed May 5, 2017 and U.S. Provisional Patent Application No. 62/614,192, filed Jan. 5, 2018, all of which are incorporated herein by reference in their entireties for all purposes.

FIELD OF THE INVENTION

The present invention relates to selecting speech features to be used for building mathematical models for detecting medical conditions to improve the performance of the models.

BACKGROUND

Early diagnosis of medical conditions, such as Alzheimer's disease or concussions, may allow for improved treatment and improved quality of life for the person with the medical condition. One method that may be used for detecting medical conditions is to process the speech of a person because the sound of a person's voice or the words used by a person may provide useful information for making a medical diagnosis.

To detect a medical condition from a person's speech, features may be extracted from the speech, and the features may be processed with a mathematical model. The type and number of features extracted from the speech may impact the performance of the model, especially where the amount of training data for training the model is limited. Accordingly, appropriate selection of features may improve the performance of the model.

BRIEF DESCRIPTION OF THE FIGURES

The invention and the following detailed description of certain embodiments thereof may be understood by reference to the following figures:

FIG. 3 is an example training corpus of speech data.

FIG. 4 is an example list of prompts for using in diagnosing a medical condition.

DETAILED DESCRIPTION

Described herein are techniques for selecting features of speech to be used to build or train a mathematical model for detecting or diagnosing a medical condition. Although the techniques described herein may be used for any appropriate medical condition, for clarity of presentation, concussions and Alzheimer's disease will be used as examples of medical conditions. The techniques described herein, however, are not limited to any particular medical conditions.

Figure 1:
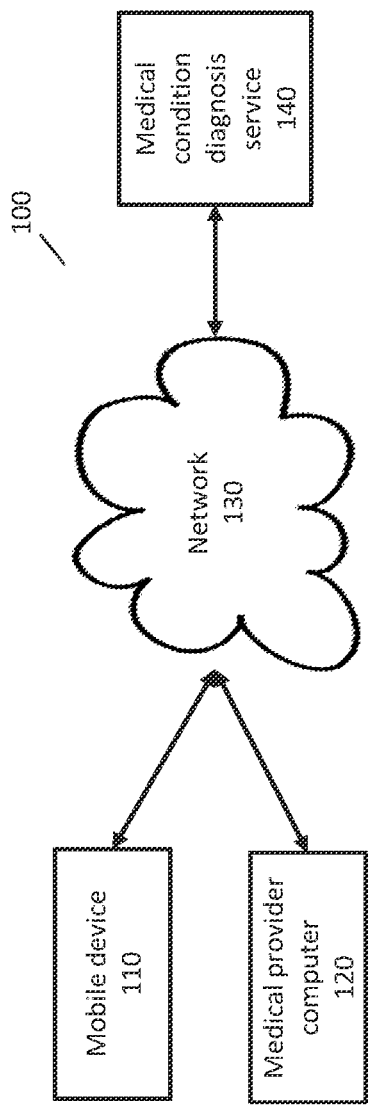
FIG. 1 is an exemplary system for providing a service for diagnosing a medical condition by processing speech of a person.

FIG. 1 is an example system 100 for diagnosing a medical condition using a person's speech. FIG. 1 includes a medical condition diagnosis service 140 that may receive speech data of a person and process the speech data to determine if a person has a medical condition. For example, medical condition diagnosis service 140 may process the speech data to compute a yes or no determination as to whether the person has the medical condition or to compute a score that indicates a probability or a likelihood that the person has the medical condition and/or a severity of the condition.

As used herein, a diagnosis relates to any determination as to whether a person may have a medical condition or any determination as to a possible severity of the medical condition. A diagnosis may include any form of an assessment, conclusion, opinion, or determination relating to a medical condition. In some instances, a diagnosis may be incorrect, and a person diagnosed with a medical condition may not actually have the medical condition.

Medical condition diagnosis service 140 may receive the speech data of a person using any appropriate techniques. For example, a person may speak to a mobile device 110 and mobile device 110 may record the speech and transmit the recorded speech data to medical condition diagnosis service 140 over network 130. Any appropriate techniques and any appropriate network may be used for mobile device 110 to transmit the recorded speech data to medical condition diagnosis service 140. For example, an application or "app" may be installed on mobile device 110 that uses a REST (representational state transfer) API (application programming interface) call to transmit the speech data over the Internet or a mobile telephone network. In another example, a medical provider may have a medical provider computer 120 that is used to record speech of a person and transmit speech data to medical condition diagnosis service 140.

In some implementations, medical condition diagnosis service 140 may be installed on mobile device 110 or medical provider computer 120 such that it is not necessary to transmit the speech data over a network. The example of FIG. 1 is not limiting, and any appropriate techniques may be used to transmit speech data for processing by a mathematical model.

The output of medical condition diagnosis service 140 may then be used for any appropriate purpose. For example, information may be presented to the person who provided the speech data or to a medical professional who is treating the person.

Figure 2:
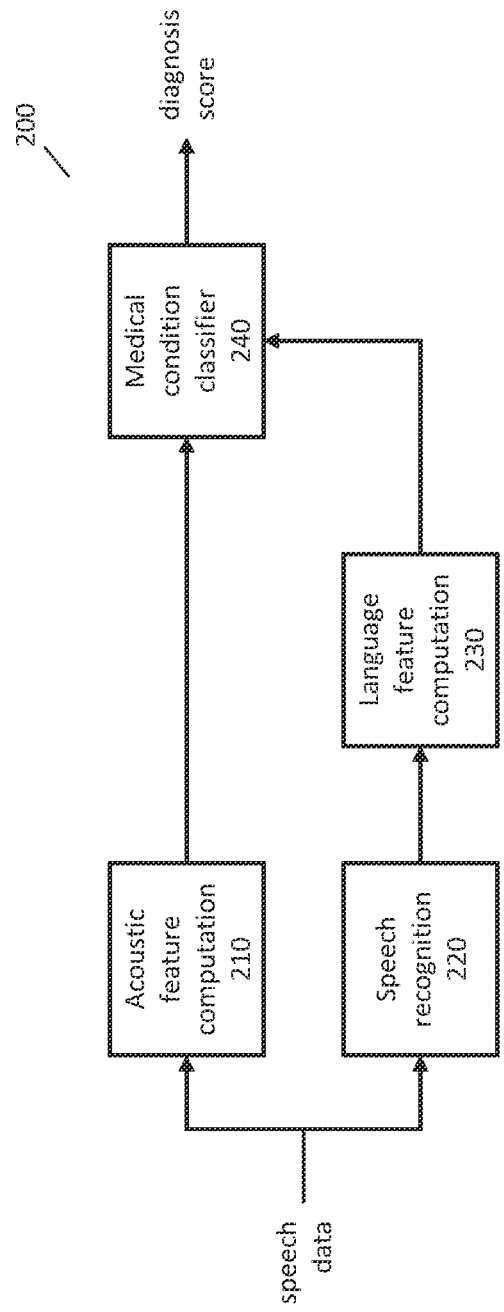
FIG. 2 is an exemplary system for processing speech data with a mathematical model to perform a medical diagnosis.

FIG. 2 is an example system 200 for processing speech data with a mathematical model to perform a medical diagnosis. In processing the speech data, features may be computed from the speech data, and then the features may be processed by the mathematical model. Any appropriate type of features may be used.

The features may include acoustic features, where acoustic features are any features computed from the speech data that do not involve or depend on performing speech recognition on the speech data (e.g., the acoustic features do not use information about the words spoken in the speech data). For example, acoustic features may include mel-frequency cepstral coefficients, perceptual linear prediction features, jitter, or shimmer.

The features may include language features where language features are computed using the results of a speech recognition. For example, language features may include a speaking rate (e.g., the number of vowels or syllables per second), a number of pause fillers (e.g., "ums" and "ahs"), the difficulty of words (e.g., less common words), or the parts of speech of words following pause fillers.

In FIG. 2, the speech data is processed by acoustic feature computation component 210 and speech recognition component 220. Acoustic feature computation component 210 may compute acoustic features from the speech data, such as any of the acoustic features described herein. Speech recognition component 220 may perform automatic speech recognition on the speech data using any appropriate techniques (e.g., Gaussian mixture models, acoustic modelling, language modelling, and neural networks).

Because speech recognition component 220 may use acoustic features in performing speech recognition, some processing of these two components may overlap and thus other configurations are possible. For example, acoustic feature component 210 may compute the acoustic features needed by speech recognition component 220, and speech recognition component 220 may thus not need to compute any acoustic features.

Language feature computation component 230 may receive speech recognition results from speech recognition component 220, and process the speech recognition results to determine language features, such as any of the language features described herein. The speech recognition results may be in any appropriate format and include any appropriate information. For example, the speech recognition results may include a word lattice that includes multiple possible sequences of words, information about pause fillers, and the timings of words, syllables, vowels, pause fillers, or any other unit of speech.

Medical condition classifier 240 may process the acoustic features and the language features with a mathematical model to output one or more diagnosis scores that indicate whether the person has the medical condition, such as a score indicating a probability or likelihood that the person has the medical condition and/or a score indicating a severity of the medical condition. Medical condition classifier 240 may use any appropriate techniques, such as a classifier implemented with a support vector machine or a neural network, such as a multi-layer perceptron.

The performance of medical condition classifier 240 may depend on the features computed by acoustic feature computation component 210 and language feature computation component 230. Further, a set of features that performs well for one medical condition may not perform well for another medical condition. For example, word difficulty may be an important feature for diagnosing Alzheimer's disease but may not be useful for determining if a person has a concussion. For another example, features relating to the pronunciation of vowels, syllables, or words may be important for Parkinson's disease but may be less important for other medical conditions. Accordingly, techniques are needed for determining a first set of features that performs well for a first medical condition, and this process may need to be repeated for determining a second set of features that performs well for a second medical condition.

In some implementations, medical condition classifier 240 may use other features, which may be referred to as non-speech features, in addition to acoustic features and language features. For example, features may be obtained or computed from demographic information of a person (e.g., gender, age, or place of residence), information from a medical history (e.g., weight, recent blood pressure readings, or previous diagnoses), or any other appropriate information.

The selection of features for diagnosing a medical condition may be more important in situations where an amount of training data for training the mathematical model is relatively small. For example, for training a mathematical model for diagnosing concussions, the needed training data may include speech data of a number of individuals shortly after they experience a concussion. Such data may exist in small quantities and obtaining further examples of such data may take a significant period of time.

Training mathematical models with a smaller amount of training data may result in overfitting where the mathematical model is adapted to the specific training data but because of the small amount of training data, the model may not perform well on new data. For example, the model may be able to detect all of the concussions in the training data, but may have a high error rate when processing production data of people who may have concussions.

One technique for preventing overfitting when training a mathematical model is to reduce the number of features used to train the mathematical model. The amount of training data needed to train a model without overfitting increases as the number of features increases. Accordingly, using a smaller number of features allows models to be built with a smaller amount of training data.

Where it is needed to train a model with a smaller number of features, it becomes more important to select the features that will allow the model to perform well. For example, when a large amount of training data is available, hundreds of features may be used to train the model and it is more likely that appropriate features have been used. Conversely, where a small amount of training data is available, only 10 or so features may be used to train a model, and it is more important to select the features that are most important for diagnosing the medical condition.

Now presented are examples of features that may be used to diagnose a medical condition.

Acoustic features may be computed using short-time segment features. When processing speech data, the duration of the speech data may vary. For example, some speech may be a second or two and other speech may be several minutes or more. For consistency in processing speech data, it may be processed in short-time segments (sometimes referred to as frames). For example, each short-time segment may be 25 milliseconds, and segments may advance in increments of 10 milliseconds so that there is a 15 millisecond overlap over two successive segments.

The following are non-limiting examples of short-time segment features: spectral features (such as mel-frequency cepstral coefficients or perceptual linear predictives); prosodic features (such as pitch, energy, or probability of voicing); voice quality features (such as jitter, jitter of jitter, shimmer, or harmonics-to-noise ratio); entropy (e.g., to capture how precisely an utterance is pronounced where entropy may be computed from the posteriors of an acoustic model that is trained on natural speech data).

The short-time segment features may be combined to compute acoustic features for the speech. For example, a two-second speech sample may produce 200 short-time segment features for pitch that may be combined to compute one or more acoustic features for pitch.

The short-time segment features may be combined to compute an acoustic feature for a speech sample using any appropriate techniques. In some implementations, an acoustic feature may be computed using statistics of the short-time segment features (e.g., arithmetic mean, standard deviation, skewness, kurtosis, first quartile, second quartile, third quartile, the second quartile minus the first quartile, the third quartile minus the first quartile, the third quartile minus the second quartile, 0.01 percentile, 0.99 percentile, the 0.99 percentile minus the 0.01 percentile, the percentage of short-time segments whose values are above a threshold (e.g., where the threshold is 75% of the range plus the minimum), the percentage of segments whose values are above a threshold (e.g., where the threshold is 90% of the range plus the minimum), the slope of a linear approximation of the values, the offset of a linear approximation of the values, the linear error computed as the difference of the linear approximation and the actual values, or the quadratic error computed as the difference of the linear approximation and the actual values. In some implementations, an acoustic feature may be computed as an i-vector or identity vector of the short-time segment features. An identity vector may be computed using any appropriate techniques, such as performing a matrix-to-vector conversion using a factor analysis technique and a Gaussian mixture model.

The following are non-limiting examples of language features. A speaking rate, such as by computing the duration of all spoken words divided by the number of vowels or any other appropriate measure of speaking rate. A number of pause fillers that may indicate hesitation in speech, such as (1) a number of pause fillers divided by the duration of spoken words or (2) a number of pause fillers divided by the number of spoken words. A measure of word difficulty or the use of less common words. For example, word difficulty may be computed using statistics of 1-gram probabilities of the spoken words, such as by classifying words according to their frequency percentiles (e.g., 5%, 10%, 15%, 20%, 30%, or 40%). The parts of speech of words following pause fillers, such as (1) the counts of each part-of-speech class divided by the number of spoken words or (2) the counts of each part-of-speech class divided by the sum of all part-of-speech counts.

In some implementations, language features may include a determination of whether a person answered a question correctly. For example, a person may be asked what the current year is or who the President of the United States is. The person's speech may be processed to determine what the person said in response to the question and to determine if the person answered the question correctly.

To train a model for diagnosing a medical condition, a corpus of training data may be collected. The training corpus may include examples of speech where the diagnosis of the person is known. For example, it may be known that the person had no concussion, or a mild, moderate, or severe concussion.

FIG. 3 illustrates an example of a training corpus that includes speech data for training a model for diagnosing concussions. For example, the rows of the table of FIG. 3 may correspond to database entries. In this example, each entry includes an identifier of a person, the known diagnosis of the person (e.g., no concussion or a mild, medium, or severe concussion), an identifier of a prompt or question that was presented to a person (e.g., "How are you today?"), and a filename of a file that contains the speech data. The training data may be stored in any appropriate format using any appropriate storage technology.

The training corpus may store a representation of a person's speech using any appropriate format. For example, a speech data item of the training corpus may include digital samples of an audio signal received at a microphone or may include a processed version of the audio signal, such as mel-frequency cepstral coefficients.

A single training corpus may contain speech data relating to multiple medical conditions, or a separate training corpus may be used for each medical condition (e.g., a first training corpus for concussions and a second training corpus for Alzheimer's disease). A separate training corpus may be used for storing speech data for people with no known or diagnosed medical condition, as this training corpus may be used for training models for multiple medical conditions.

FIG. 4 illustrates an example of stored prompts that may be used to diagnose medical conditions. Each prompt may be presented to a person, either by a person (e.g., a medical professional) or a computer, to obtain speech of the person in response to the prompt. Each prompt may have a prompt identifier so that it may be cross referenced with the prompt identifier of the training corpus. The prompts of FIG. 4 may be stored using any appropriate storage technology, such as a database.

Figure 5:
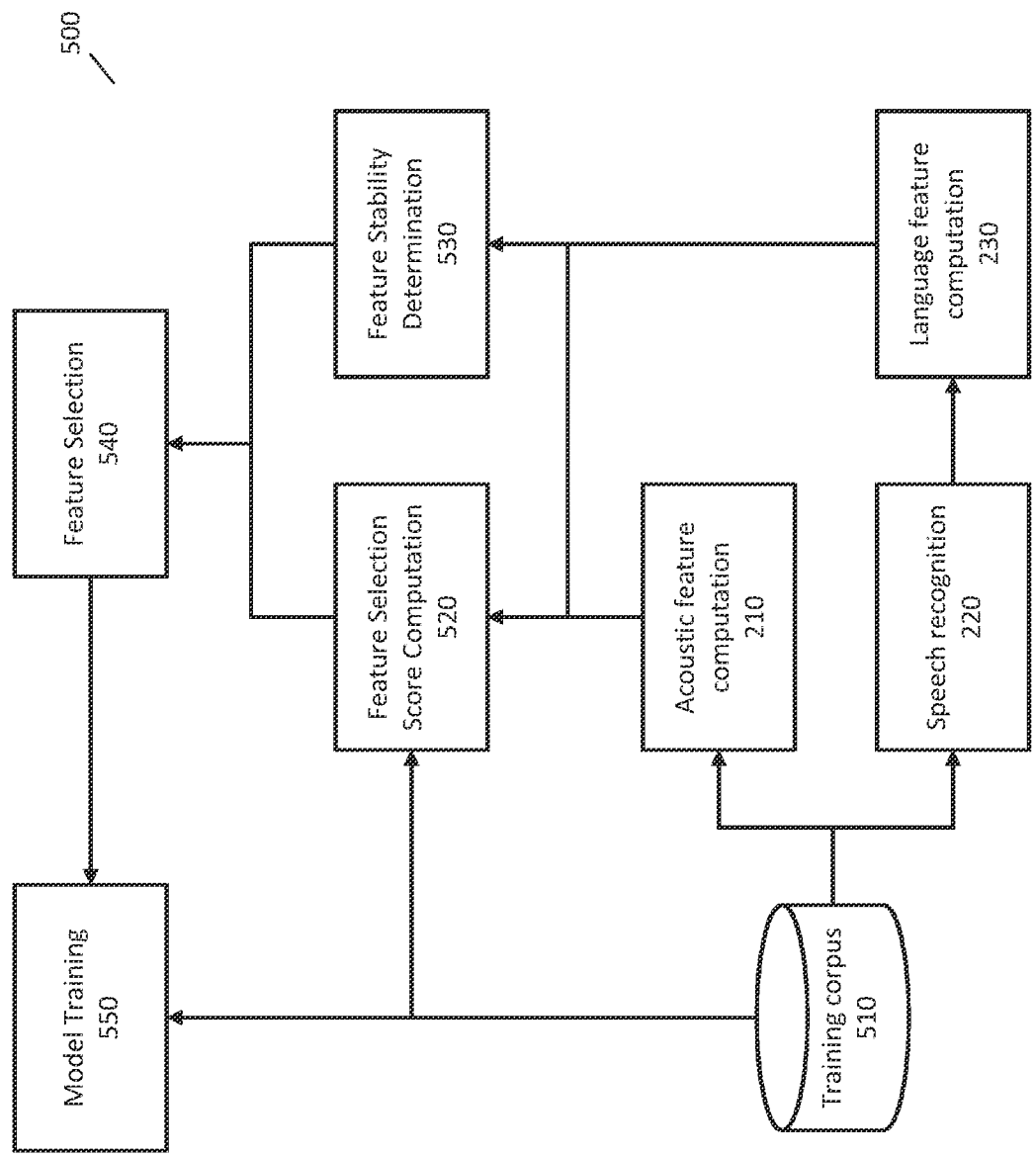
FIG. 5 is an exemplary system for selecting features for training a mathematical model for diagnosing a medical condition.

FIG. 5 is an exemplary system 500 that may be used to select features for training a mathematical model for diagnosing a medical condition, and then using the selected features to train the mathematical model. System 500 may be used multiple times to select features for different medical conditions. For example, a first use of system 500 may select features for diagnosing concussions and a second use of system 500 may select features for diagnosing Alzheimer's disease.

FIG. 5 includes a training corpus 510 of speech data items for training a mathematical model for diagnosing a medical condition. Training corpus 510 may include any appropriate information, such as speech data of multiple people with and without the medical condition, a label indicating whether or not person has the medical condition, and any other information described herein.

Acoustic feature computation component 210, speech recognition component 220, and language feature computation component 230 may be implemented as described above to compute acoustic and language features for the speech data in the training corpus. Acoustic feature computation component 210 and language feature computation component 230 may compute a large number of features so that the best performing features may be determined. This may be in contrast to FIG. 2 where these components are used in a production system and thus these components may compute only the features that were previously selected.

Feature selection score computation component 520 may compute a selection score for each feature (which may be an acoustic feature, a language feature, or any other feature described herein). To compute a selection score for a feature, a pair of numbers may be created for each speech data item in the training corpus, where the first number of the pair is the value of the feature and the second number of the pair is an indicator of the medical condition diagnosis. The value for the indicator of the medical condition diagnosis may have two values (e.g., 0 if the person does not have the medical condition and 1 if the person has the medical condition) or may have a larger number of values (e.g., a real number between 0 and 1 or multiple integers indicating a likelihood or severity of the medical condition).

Figure 6B:
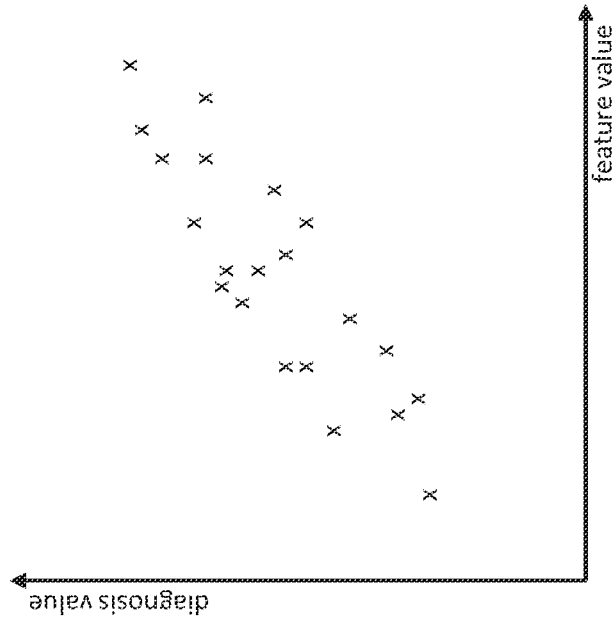
FIGS. 6A and 6B are conceptual graphs of pairs of feature values and diagnosis values.
Figure 6A:
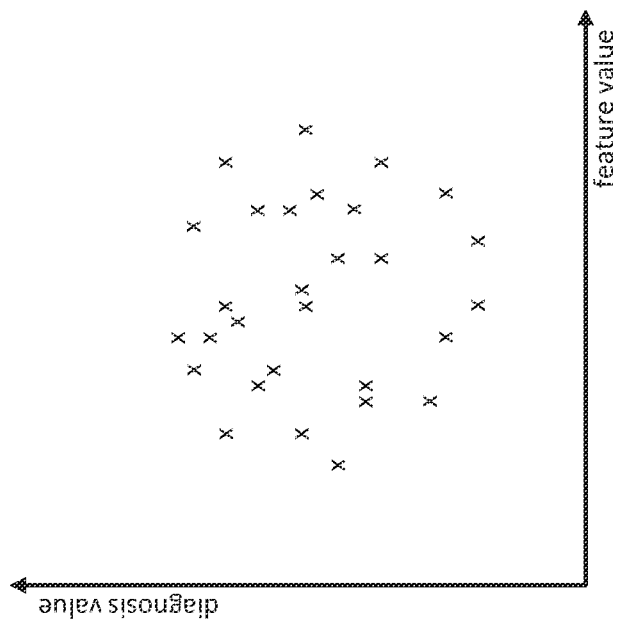

Accordingly, for each feature, a pair of numbers may be obtained for each speech data item of the training corpus. FIGS. 6A and 6B illustrate two conceptual plots of the pairs of numbers for a first feature and a second feature. For FIG. 6A, there does not appear to be a pattern or correlation between the values of the first feature and the corresponding diagnosis values, but for FIG. 6B, there does appear to be a pattern or correlation between the values of the second feature and the diagnosis values. Accordingly, one may conclude that the second feature is likely a useful feature for determining whether a person has the medical condition and that the first feature is not.

Feature selection score computation component 520 may compute a selection score for a feature using the pairs of feature values and diagnosis values. Feature selection score computation component 520 may compute any appropriate score that indicates a pattern or correlation between the feature values and the diagnosis values. For example, feature selection score computation component 520 may compute a Rand index, an adjusted Rand index, mutual information, adjusted mutual information, a Pearson correlation, an absolute Pearson correlation, a Spearman correlation, or an absolute Spearman correlation.

The selection score may indicate the usefulness of the feature in detecting a medical condition. For example, a high selection score may indicate that a feature should be used in training the mathematical model, and a low selection score may indicate that the feature should not be used in training the mathematical model.

Feature stability determination component 530 may determine if a feature (which may be an acoustic feature, a language feature, or any other feature described herein) is stable or unstable. To make a stability determination, the speech data items may be divided into multiple groups, which may be referred to as folds. For example, the speech data items may be divided into five folds. In some implementations, the speech data items may be divided into folds such that each fold has an approximately equal number of speech data items for different genders and age groups.

The statistics of each fold may be compared to statistics of the other folds. For example, for a first fold, the median (or mean or any other statistic relating to the center or middle of a distribution) feature value (denoted as $M_1$) may be determined. Statistics may also be computed for the combination of the other folds. For example, for the combination of the other folds, the median of the feature values (denoted as $M_o$ and a statistic measuring of variability of the feature values (denoted as VA such as interquartile range, variance, or standard deviation, may be computed. The feature may be determined to be unstable if the median of the first fold differs too greatly from the median of the second fold. For example, the feature may be determined to be unstable if $$M_1 < M_o - C\frac{V_o}{2} \text{ or } M_1 > M_o + C\frac{V_o}{2}$$

where C is a scaling factor. The process may then be repeated for each of the other folds. For example, the median of a second fold may be compared with median and variability of the other folds as described above.

In some implementations, if, after comparing each fold to the other folds, the median of each fold is not too far from the median of the other folds, then the feature may be determined to be stable. Conversely, if the median of any fold is too far from the median of the other folds, then the feature may be determined to be unstable.

In some implementations, feature stability determination component 530 may output a boolean value for each feature to indicate whether the feature is stable or not. In some implementations, stability determination component 530 may output a stability score for each feature. For example, a stability score may be computed as largest distance between the median of a fold and the other folds (e.g., a Mahalanobis distance).

Feature selection component 540 may receive the selection scores from feature selection score computation component 520 and the stability determinations from feature stability determination component 530 and select a subset of features to be used to train the mathematical model. Feature selection component 540 may select a number of features having the highest selection scores that are also sufficiently stable.

In some implementations, the number of features to be selected (or a maximum number of features to be selected) may be set ahead of time. For example, a number N may be determined based on the amount of training data, and N features may be selected. The selected features may be determined by removing unstable features (e.g., features determined to be unstable or features with a stability score below a threshold) and then selecting the N features with the highest selection scores.

In some implementations, the number of features to be selected may be based on the selection scores and stability determinations. For example, the selected features may be determined by removing unstable features, and then selecting all features with a selection score above a threshold.

In some implementations, the selection scores and stability scores may be combined when selecting features. For example, for each feature a combined score may be computed (such as by adding or multiplying the selection score and the stability score for the feature) and features may be selected using the combined score.

Model training component 550 may then train a mathematical model using the selected features. For example, model training component 550 may iterate over the speech data items of the training corpus, obtain the selected features for the speech data items, and then train the mathematical model using the selected features. In some implementations, dimension reduction techniques, such as principal components analysis or linear discriminant analysis, may be applied to the selected features as part of the model training. Any appropriate mathematical model may be trained, such as any of the mathematical models described herein.

In some implementations, other techniques, such as wrapper methods, may be used for feature selection or may be used in combination with the feature selection techniques presented above. Wrapper methods may select a set of features, train a mathematical model using the selected set of features, and then evaluate the performance of the set of features using the trained model. Where the number of possible features is relatively small and/or training time is relatively short, all possible sets of features may be evaluated and the best performing set may be selected. Where the number of possible features is relatively large and/or the training time is a significant factor, optimization techniques may be used to iteratively find a set of features that performs well. In some implementations, a set of features may be selected using system 500, and then a subset of these features may be selected using wrapper methods as the final set of features.

Figure 7:
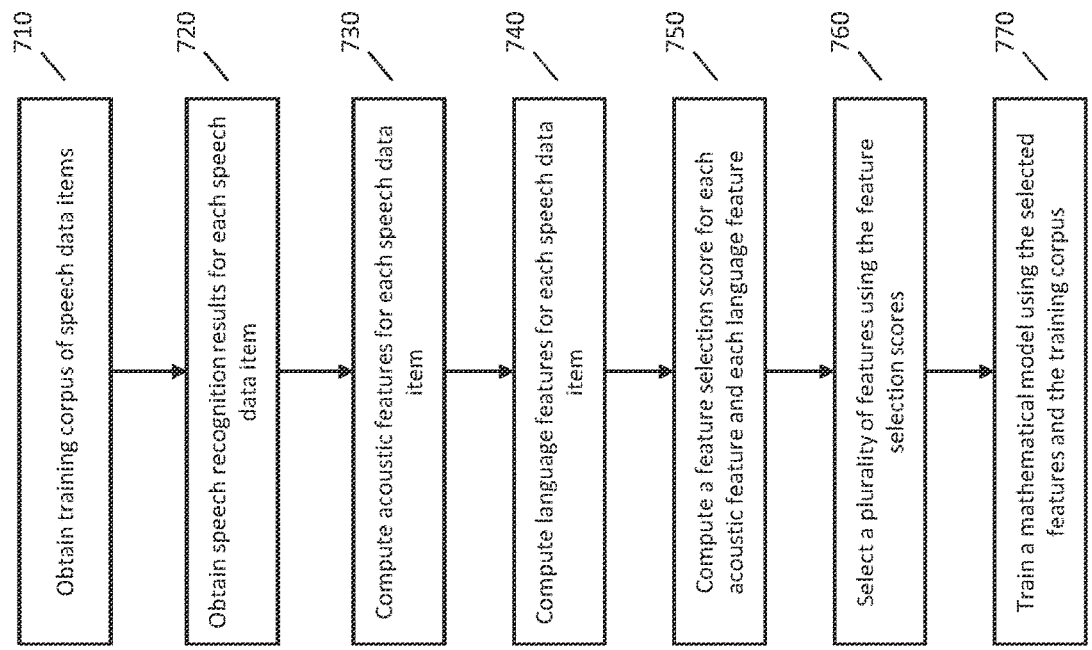
FIG. 7 is a flowchart of an example implementation of selecting features for training a mathematical model for diagnosing a medical condition.

FIG. 7 is a flowchart of an example implementation of selecting features for training a mathematical model for diagnosing a medical condition. In FIG. 7 and other flowcharts herein, the ordering of the steps is exemplary and other orders are possible, not all steps are required, steps may be combined (in whole or part) or sub-divided and, in some implementations, some steps may be omitted or other steps may be added. The methods described by any flowcharts described herein may be implemented, for example, by any of the computers or systems described herein.

At step 710, a training corpus of speech data items is obtained. The training corpus may include a representation of an audio signal of a person's speech, an indication of a medical diagnosis of the person from whom the speech was obtained, and any other appropriate information, such as any of the information described herein.

At step 720, speech recognition results are obtained for each speech data item of the training corpus. The speech recognition results may have been computed in advance and stored with the training corpus or stored in another location. The speech recognition results may include any appropriate information, such as a transcript, a list of highest scoring transcripts (e.g., an N-best list), a lattice of possible transcriptions, and timing information, such as the start and end time of words, pause fillers, or other speech units.

At step 730, acoustic features are computed for each speech data item of the training corpus. Acoustic features may include any features that are computed without using speech recognition results of a speech data item, such as any of the acoustic features described herein. Acoustic features may include or be computed from data used in the speech recognition process (e.g., mel-frequency cepstral coefficients or perceptual linear predictors), but acoustic features do not use speech recognition results, such as information about the words or pause fillers present in a speech data item.

At step 740, language features are computed for each speech data item of the training corpus. Language features may include any features that are computed using speech recognition results, such as any of the language features described herein.

At step 750, a feature selection score is computed for each acoustic feature and each language feature. To compute a feature selection score for the feature, the value of the feature for each speech data item in the training corpus may be used along with other information, such as a known diagnosis value corresponding to the speech data item. The feature selection score may be computed using any of the techniques described herein, such as by computing an absolute Pearson correlation. In some implementations, feature selection scores may be computed for other features as well, such as features relating to demographic information of a person.

At step 760, a plurality of features is selected using the feature selection scores. For example, a number of features having the highest selection scores may be selected. In some implementations, a stability determination may be computed for each feature and the plurality of features may be selected using both the feature selection scores and the stability determinations, such as by using any of the techniques described herein.

At step 770, a mathematical model is trained using the selected features. Any appropriate mathematical model may be trained, such as a neural network or a support vector machine. After the mathematical model has been trained, it may be deployed in a production system, such as system 100 of FIG. 1 to perform diagnosis of medical conditions.

The steps of FIG. 7 may be performed in a variety of manners. For example, in some implementations, steps 730, and 740 may be performed in a loop that loops over each of the speech data items in the training corpus. For a first iteration, acoustic and language features may be computed for a first speech data item, for a second iteration, acoustic and language features may be computed for a second speech data item, and so forth.

When using a deployed model for diagnosing a medical condition, the person being diagnosed may be presented with a sequence of prompts or questions to obtain speech from the person. Any appropriate prompts may be used, such as any of the prompts of FIG. 4. After the features have been selected, as described above, prompts may be selected so that the selected prompts provide useful information about the selected features.

For example, suppose that a selected feature is pitch. While pitch has been determined to be a useful feature for diagnosing a medical condition, some prompts may be better than others in obtaining a useful pitch feature. Very short utterances (e.g., yes/no answers) may not provide sufficient data to accurately compute pitch and thus prompts that generate longer responses may be more useful in obtaining information about pitch.

For another example, suppose that a selected feature is word difficulty. While word difficulty has been determined to be a useful feature for diagnosing a medical condition, some prompts may be better than others in obtaining a useful word difficulty feature. Prompts that ask a user to read a presented passage will generally result in speech of the words in the passage, and thus the word difficulty feature would have the same value each time this prompt is presented, and thus this prompt would not be useful in obtaining information about word difficulty. By contrast, open ended questions, such as "Tell me about your day?", may result in greater variability of vocabulary in responses and thus may provide more useful information about word difficulty.

Selecting a set of prompts may also improve the performance of a system for diagnosing medical conditions and provide a better experience for the person being evaluated. By using the same set of prompts for each person being evaluated, the system for diagnosing medical conditions may provide more accurate results, since the data collected from multiple people may be more comparable than if different prompts were used with each person. Further, using a defined set of prompts, allows the evaluation of a person to be more predictable and of a desired duration that is appropriate for the evaluation of the medical condition. For example, for evaluating whether a person has Alzheimer's disease, it may be acceptable to use more prompts to collect a larger amount of data, but for evaluating whether a person has a concussion during a sporting event, it may be necessary to use a smaller number of prompts to obtain a result more quickly.

In some implementations, prompts may be selected by computing prompt selection scores. A training corpus may have multiple or even many speech data items for a single prompt. For example, the training corpus may include examples of the prompt used with different people or the same prompt may be used with the same person multiple times.

Figure 8:
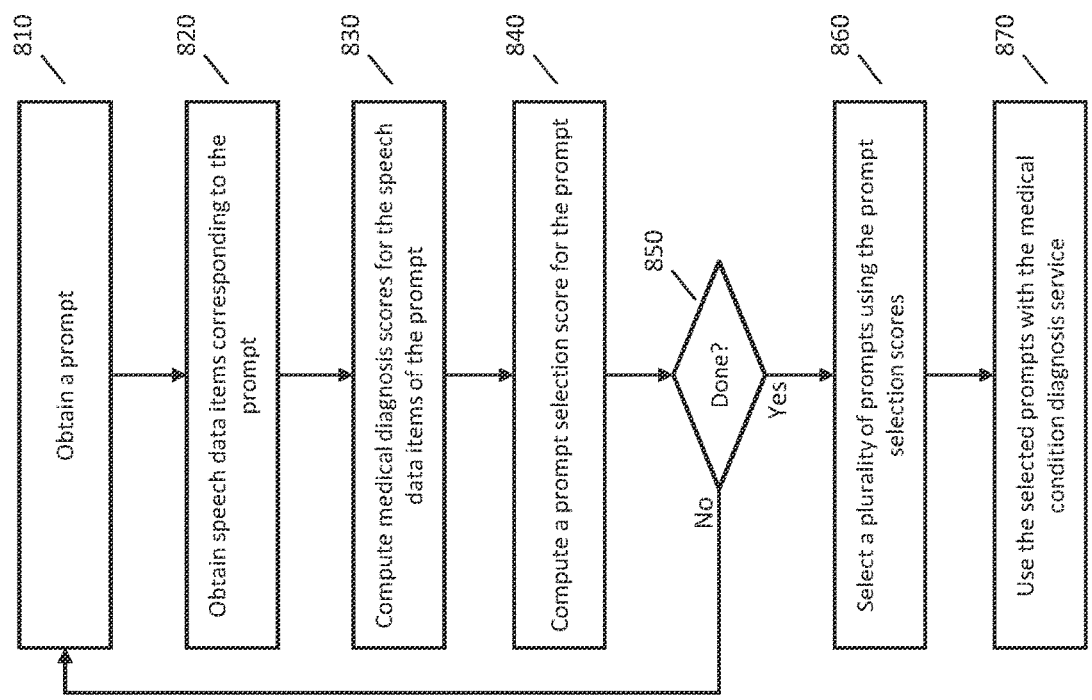
FIG. 8 is a flowchart of an example implementation of selecting prompts for use with a mathematical model for diagnosing a medical condition.

FIG. 8 is a flowchart of an example implementation of selecting prompts for use with a deployed model for diagnosing a medical condition.

Steps 810 to 840 may be performed for each prompt (or a subset of the prompts) in the training corpus to compute a prompt selection score for each prompt.

At step 810 a prompt is obtained, and at step 820 speech data items corresponding to the prompt are obtained from the training corpus.

At step 830, a medical diagnosis score is computed for each speech data item corresponding to the prompt. For example, a medical diagnosis score for a speech data item may be a number output by a mathematical model (e.g., the mathematical model trained in FIG. 7) indicating a likelihood that a person has the medical condition and/or a severity of the medical condition.

At step 840, a prompt selection score is computed for the prompt using the computed medical diagnosis scores. The computation of a prompt selection score may be similar to the computation of a feature selection score, as described above. For each speech data item corresponding to the prompt, a pair of numbers may be obtained. For each pair, the first number of the pair may be the computed medical diagnosis score computed from the speech data item, and the second number of the pair may be a known medical condition diagnosis of the person (e.g., the person is known to have the medical condition or a severity of the medical condition). Plotting these pairs of numbers may result in a plot similar to FIG. 6A or FIG. 6B, and depending on the prompt there may or may not be a pattern or correlation in the pairs of numbers.

A prompt selection score for a prompt may include any score that indicates a pattern or correlation between the computed medical diagnosis scores and the known medical condition diagnoses. For example, a prompt selection score may include a Rand index, an adjusted Rand index, mutual information, adjusted mutual information, a Pearson correlation, an absolute Pearson correlation, a Spearman correlation, or an absolute Spearman correlation.

At step 850 it is determined if other prompts remain to be processed. If prompts remain to be processed, then processing may proceed to step 810 to process additional prompts. If all prompts have been processed, then processing may proceed to step 860.

At step 860, a plurality of prompts is selected using the prompt selection scores. For example, a number of prompts having the highest prompt selection scores may be selected. In some implementations, a stability determination may be computed for each prompt and the plurality of prompts may be selected using both the prompt selection scores and the prompt stability determinations, such as by using any of the techniques described herein.

At step 870, the selected prompts are used with a deployed medical condition diagnosis service. For example, when diagnosing a person, the selected prompts may be presented to a person to obtain speech of the person in response to each of the prompts.

In some implementations, other techniques, such as wrapper methods, may be used for prompt selection or may be used in combination with the prompt selection techniques presented above. In some implementations, a set of prompts may be selected using the process of FIG. 8, and then a subset of these prompts may be selected using wrapper methods as the final set of features.

In some implementations, a person involved with creating the medical condition diagnosis service may assist in the selection of prompts. The person may use his knowledge or experience to select prompts based on the selected features. For example, where a selected feature is word difficulty, the person may review the prompts and select prompts that are more likely to provide useful information relating to word difficulty. The person may select one or more prompts that are likely to provide useful information for each of the selected features.

In some implementations, the person may review the prompts selected by the process of FIG. 8, and add or remove prompts to improve the performance of a medical condition diagnosis system. For example, two prompts may each provide useful information about word difficulty, but the information provided by the two prompts may be largely redundant, and using both prompts may not provide significant benefit over using just one of them.

In some implementations, a second mathematical model may be trained after prompt selection that is adapted to the selected prompts. The mathematical model trained in FIG. 7 may process a single utterance (in response to a prompt) to generate a medical diagnosis score. Where the process of performing a diagnosis comprises processing multiple utterances corresponding to multiple prompts, then each of the utterances may be processed by the mathematical model of FIG. 7 to generate multiple medical diagnosis scores. To determine an overall medical diagnosis, the multiple medical diagnosis scores may need to be combined in some way. Accordingly, the mathematical model trained in FIG. 7 may not be adapted to a selected set of prompts.

When the selected prompts are used in a session to diagnose a person, each of the prompts may be presented to the person to obtain an utterance corresponding to each of the prompts. Instead of processing the utterances separately, the utterances may be processed simultaneously by the model to generate a medical diagnosis score. Accordingly, a model may be adapted to the selected prompts because it is trained to simultaneously process utterances corresponding to each of the selected prompts.

Figure 9:
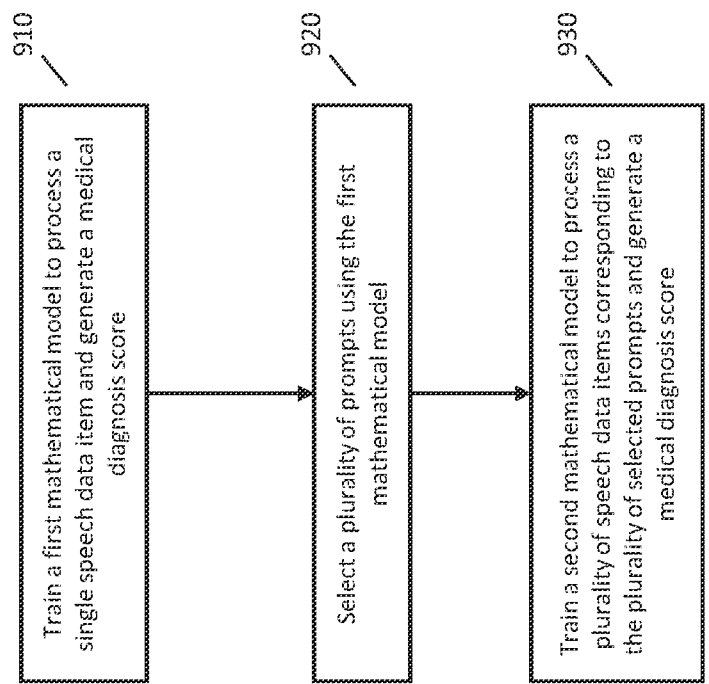
FIG. 9 is a flowchart of an example implementation of training a mathematical model for diagnosing a medical condition that is adapted to a set of selected prompts.

FIG. 9 is a flowchart of an example implementation training a mathematical model that is adapted to a set of selected prompts. At step 910, a first mathematical model is obtained, such as by using the process of FIG. 7. At step 920, a plurality of prompts is selected using the first mathematical model, such as by the process of FIG. 8.

At step 930, a second mathematical model is trained that simultaneously processes multiple speech data items corresponding to the plurality of selected prompts to generate a medical diagnosis score. When training the second mathematical model, a training corpus may be used that includes sessions with speech data items corresponding to each of the plurality of selected prompts. When training the mathematical model, the input to the mathematical model may be fixed to the speech data items from the session and corresponding to each of the selected prompts. The output of the mathematical model may be fixed to a known medical diagnosis. The parameters of the model may then be trained to optimally process the speech data item simultaneously to generate a medical diagnosis score. Any appropriate training techniques may be used, such as stochastic gradient descent.

The second mathematical model may then be deployed as part of a medical condition diagnosis service, such as the service of FIG. 1. The second mathematical model may provide better performance than the first mathematical model because it has been trained to process the utterances simultaneously rather than individual and thus the training may be better able to combine the information from all the of utterances to generate the medical condition diagnosis score.

Figure 10:
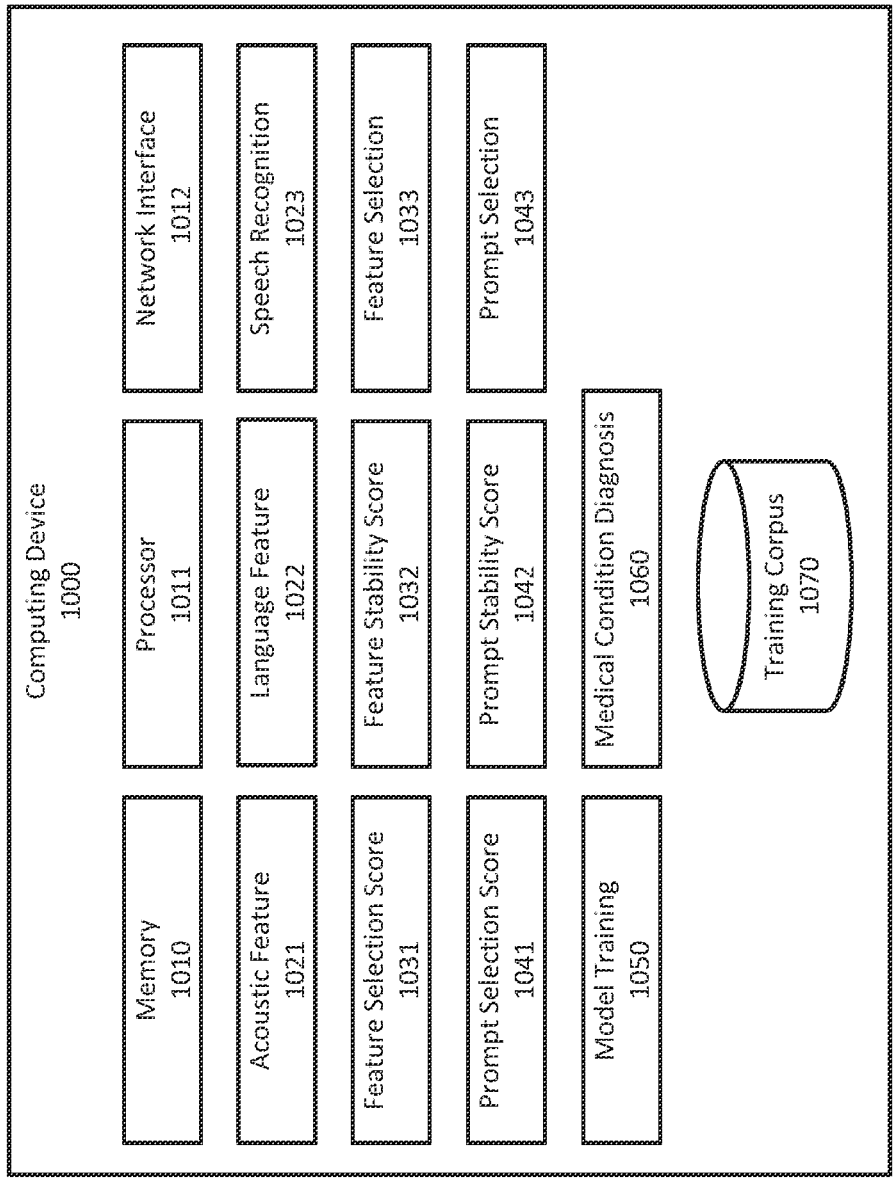
FIG. 10 is an exemplary computing device that may be used to train and deploy a mathematical model for diagnosing a medical condition.

FIG. 10 illustrates components of one implementation of a computing device 1000 for implementing any of the techniques described above. In FIG. 10, the components are shown as being on a single computing device, but the components may be distributed among multiple computing devices, such as a system of computing devices, including, for example, an end-user computing device (e.g., a smart phone or a tablet) and/or a server computing device (e.g., cloud computing).

Computing device 1000 may include any components typical of a computing device, such as volatile or nonvolatile memory 1010, one or more processors 1011, and one or more network interfaces 1012. Computing device 1000 may also include any input and output components, such as displays, keyboards, and touch screens. Computing device 1000 may also include a variety of components or modules providing specific functionality, and these components or modules may be implemented in software, hardware, or a combination thereof. Below, several examples of components are described for one example implementation, and other implementations may include additional components or exclude some of the components described below.

Computing device 1000 may have an acoustic feature computation component 1021 that may compute acoustic features for a speech data item as described above. Computing device 1000 may have a language feature computation component 1022 that may compute language features for a speech data item as described above. Computing device 1000 may have a speech recognition component 1023 that may generate speech recognition results for a speech data item as described above. Computing device 1000 may have a feature selection score computation component 1031 that may compute selection scores for features as described above. Computing device 1000 may have a feature stability score computation component 1032 that may make stability determinations or compute stability scores as described above. Computing device 1000 may have a feature selection component 1033 that may select features using selection scores and/or stability determinations as described above. Computing device 1000 may have a prompt selection score computation component 1041 that may compute selection scores for prompts as described above. Computing device 1000 may have a prompt stability score computation component 1042 that may make stability determinations or compute stability scores as described above. Computing device 1000 may have a prompt selection component 1043 that may select prompts using selection scores and/or stability determinations as described above. Computing device 1000 may have a model training component 1050 that may train mathematical models as described above. Computing device 1000 may have a medical condition diagnosis component 1060 that may process speech data items to determine a medical diagnosis score as described above.

Computing device 1000 may include or have access to various data stores, such as training corpus data store 1070. Data stores may use any known storage technology such as files, relational or non-relational databases, or any non-transitory computer-readable media.

The methods and systems described herein may be deployed in part or in whole through a machine that executes computer software, program codes, and/or instructions on a processor. "Processor" as used herein is meant to include at least one processor and unless context clearly indicates otherwise, the plural and the singular should be understood to be interchangeable. Any aspects of the present disclosure may be implemented as a method on the machine, as a system or apparatus as part of or in relation to the machine, or as a computer program product embodied in a computer readable medium executing on one or more of the machines. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

What is claimed is:

1. A system for training a mathematical model for detecting a medical condition, the system comprising at least one computer configured to:

obtain a training corpus comprising speech data items, wherein each speech data item is labelled with a diagnosis value;

compute a plurality of features for each speech data item in the training corpus;

select a subset of the plurality of features based on, for each speech data item, the diagnosis value corresponding to the speech data item and a usefulness of the feature for detecting the medical condition;

train the mathematical model for detecting the medical condition using the subset of the plurality of features for each speech data item of the training corpus;

deploy a computer program product or computer service for detecting the medical condition using the mathematical model;

present, by the computer program product or computer service, a prompt to a person;

receive, by the computer program product or computer service, a speech data item corresponding to speech of a person in response to the prompt;

compute a medical diagnosis by processing the received speech data item using the mathematical model; and display, by the computer program product or computer service, the medical diagnosis.

2. The system of claim 1, wherein the at least one computer is configured to:

obtain speech recognition results for each speech data item of the training corpus, wherein the speech recognition results for a speech data item comprise a transcription of the speech data item;

compute a language feature for each speech data item in the training corpus by processing the speech recognition results; and wherein the plurality of features comprise the language feature.

3. The system of claim 1, wherein each speech data item of the training corpus corresponds to a prompt of a plurality of prompts, the plurality of prompts comprising the presented prompt, and wherein the at least one computer is configured to:

compute a medical diagnosis score for each speech data item of the training corpus by processing the speech data items with the mathematical model;

compute a prompt selection score for each prompt of the plurality of prompts using the medical diagnosis scores;

select a subset of prompts from the plurality of prompts using the prompt selection scores, the subset of prompts comprising the presented prompt;

deploy the computer program product or computer service for detecting the medical condition using the mathematical model and the subset of prompts;

receive a speech data item corresponding to speech of the person for each prompt of the subset of prompts; and compute the medical diagnosis for the person by processing the received speech data items using the mathematical model.

4. The system of claim 1, wherein the at least one computer is configured to:

compute an acoustic feature for each speech data item in the training corpus, wherein the acoustic feature is computed from the speech data item and wherein computation of the acoustic feature does not use speech recognition results of the speech data item; and
wherein the plurality of features comprise the acoustic feature.

5. The system of claim 4, wherein the plurality of features comprise a language feature computed from speech recognition results of a speech data item.

6. The system of claim 1, wherein the mathematical model comprises a neural network or a support vector machine.

7. The system of claim 1, wherein the plurality of features comprises at least one of spectral features, prosodic features, or voice quality features.

8. A computer-implemented method for training a mathematical model for detecting a medical condition, the method comprising:
   obtaining a training corpus comprising speech data items, wherein each speech data item is labelled with a diagnosis value;
   computing a plurality of features for each speech data item in the training corpus;
   selecting a subset of the plurality of features based on, for each speech data item, the diagnosis value corresponding to the speech data item and a usefulness of the feature for detecting the medical condition;
   training the mathematical model for detecting the medical condition using the subset of the plurality of features for each speech data item of the training corpus;
   deploying a computer program product or computer service for detecting the medical condition using the mathematical model;
   presenting, by the computer program product or computer service, a prompt to a person;
   receiving, by the computer program product or computer service, a speech data item corresponding to speech of a person in response to the prompt;
   computing a medical diagnosis by processing the received speech data item using the mathematical model; and
   displaying, by the computer program product or computer service, the medical diagnosis.

9. The computer-implemented method of claim 8, wherein the medical condition is a concussion or Alzheimer's disease.

10. The computer-implemented method of claim 8, wherein the plurality of features comprises one or more of a number of pause fillers over a period of time, a number of pause fillers over a number of words, word difficulty, or speaking rate.

11. The computer-implemented method of claim 8, further comprising computing a feature selection score for a feature by generating a pair of numbers for each speech data item of the training corpus, and wherein a first number of the pair corresponds to a feature value and a second number of the pair corresponds to a diagnosis value.

12. The computer-implemented method of claim 8, comprising:
   dividing the training corpus into a plurality of folds; and
   computing a statistic for each feature and each fold of the plurality of folds.

13. The computer-implemented method of claim 12, comprising:
   computing a stability determination for each feature of the plurality of features using the statistics for each feature and each fold of the plurality of folds; and
   selecting the subset of the plurality of features using the stability determinations.

14. The computer-implemented method of claim 8, comprising:
   selecting a plurality of prompts using the mathematical model; and
   training a second mathematical model using the selected plurality of prompts and the speech data items of the training corpus.

15. One or more non-transitory computer-readable media comprising computer executable instructions that, when executed, cause at least one processor to perform actions comprising:
   obtaining a training corpus comprising speech data items, wherein each speech data item is labelled with a diagnosis value;
   obtaining a plurality of features for each speech data item in the training corpus;
   selecting a subset of the plurality of features based on, for each speech data item, the diagnosis value corresponding to the speech data item and a usefulness of the feature for detecting the medical condition;
   training a mathematical model for detecting the medical condition using the subset of the plurality of features for each speech data item of the training corpus;
   deploying a computer program product or computer service for detecting the medical condition using the mathematical model;
   presenting, by the computer program product or computer service, a prompt to a person;
   receiving, by the computer program product or computer service, a speech data item corresponding to speech of a person in response to the prompt;
   computing a medical diagnosis by processing the received speech data item using the mathematical model; and
   displaying, by the computer program product or computer service, the medical diagnosis.

16. The one or more non-transitory computer-readable media of claim 15, wherein computing a first feature of the plurality of features comprises:
   computing a value for each short-time segment of an audio signal to obtain a plurality of values; and
   computing the first feature using the plurality of values.

17. The one or more non-transitory computer-readable media of claim 15, wherein the actions comprise computing a feature selection score for each feature of the plurality of features wherein the feature selection score comprises an adjusted Rand index, adjusted mutual information, an absolute Pearson correlation, or an absolute Spearman correlation.

18. The one or more non-transitory computer-readable media of claim 15, wherein the actions comprise:
   computing a stability determination for each feature of the plurality of features; and
   selecting the plurality of features using the stability determinations.

19. The one or more non-transitory computer-readable media of claim 15, wherein each speech data item of the training corpus corresponds to a prompt of a plurality of prompts, the plurality of prompts comprising the presented prompt, and wherein the actions comprise:
   computing a medical diagnosis score for each speech data item of the training corpus by processing the speech data items with the mathematical model;
   computing a prompt selection score for each prompt of the plurality of prompts using the medical diagnosis scores;
   selecting a subset of prompts from the plurality of prompts using the prompt selection scores, the subset of prompts comprising the presented prompt; and deploying the computer program product or computer service for detecting the medical condition using the mathematical model and the subset of prompts.

20. The one or more non-transitory computer-readable media of claim 15, wherein the plurality of features comprise a non-speech feature.

* * * * *